United States Patent [19]

Humphrey

[11] Patent Number: 4,732,466

[45] Date of Patent: Mar. 22, 1988

[54] FUNDUS CAMERA

[75] Inventor: William E. Humphrey, Oakland, Calif.

[73] Assignee: Humphrey Instruments, Inc., San Leandro, Calif.

[21] Appl. No.: 719,779

[22] Filed: Apr. 4, 1985

[51] Int. Cl.⁴ ............................. A61B 3/14; A61B 3/10
[52] U.S. Cl. ..................................... 351/206; 351/211; 351/221
[58] Field of Search .............. 351/206, 207, 208, 211, 351/221; 354/62; 350/6.91, 6.8

[56] References Cited

U.S. PATENT DOCUMENTS

| | | | |
|---|---|---|---|
| 3,547,512 | 4/1968 | Baer | 350/6.91 |
| 3,819,256 | 6/1974 | Bellows et al. | 351/211 |
| 3,888,569 | 6/1975 | Munnerly et al. | 351/211 |
| 4,526,451 | 7/1985 | Nohda | 351/211 |
| 4,579,430 | 4/1986 | Bille | 351/206 |

Primary Examiner—Rodney B. Bovernick
Attorney, Agent, or Firm—Townsend & Townsend

[57] ABSTRACT

An optical system for forming an image of the retina of the human eye. The system includes a rotating drum having transmission/receiving slit pairs formed thereon. The rotation of the drum scans an illumination region and viewing beam across the retina. Embodiments for forming stereo images, for synchronizing the formation of the image of the retina with the sweep of a vidicon tube, for automatically focusing the system, for providing flare control, for providing displaced slit functions, and for providing multiple functions are included.

16 Claims, 12 Drawing Figures

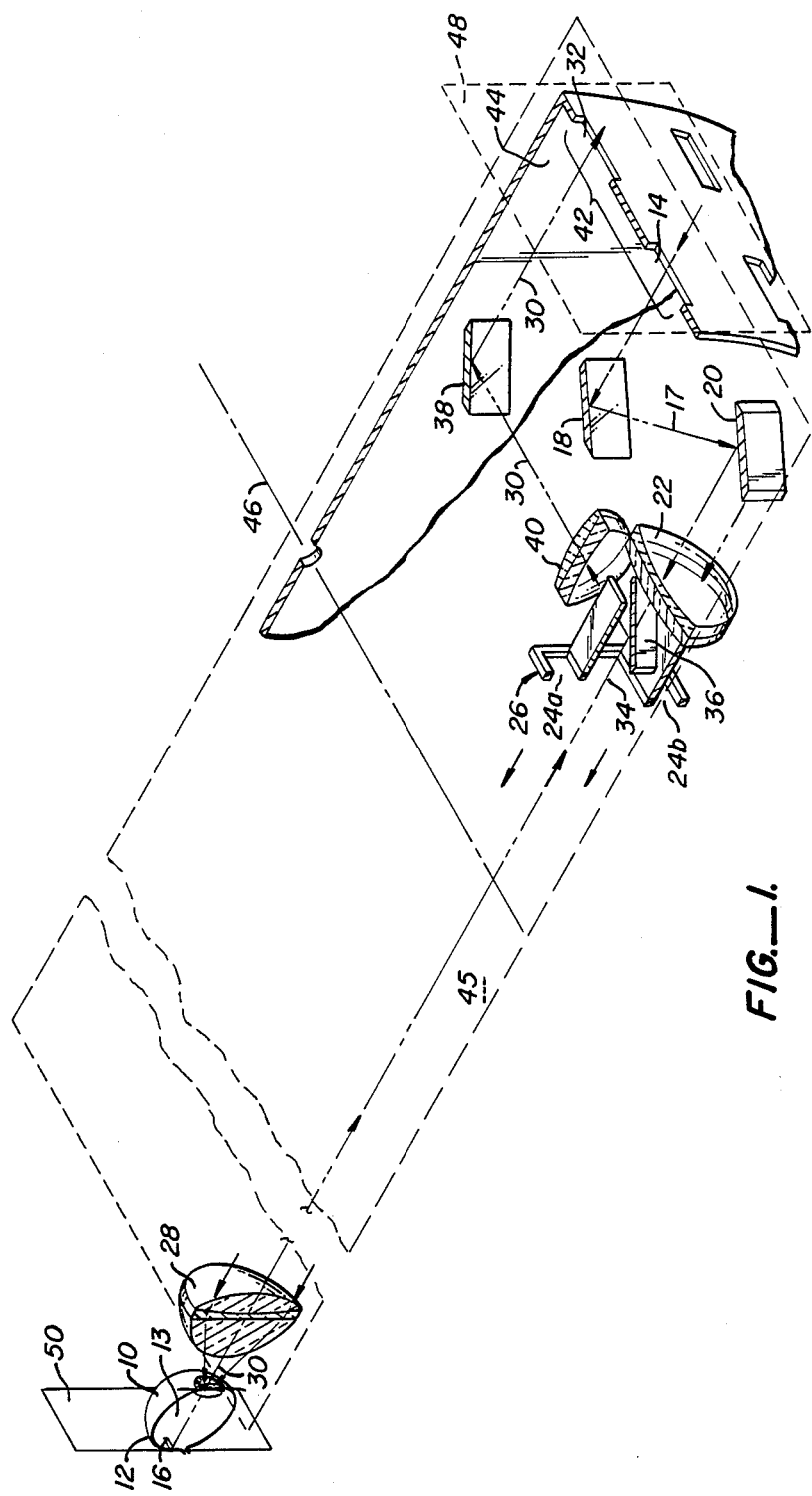
FIG._1.

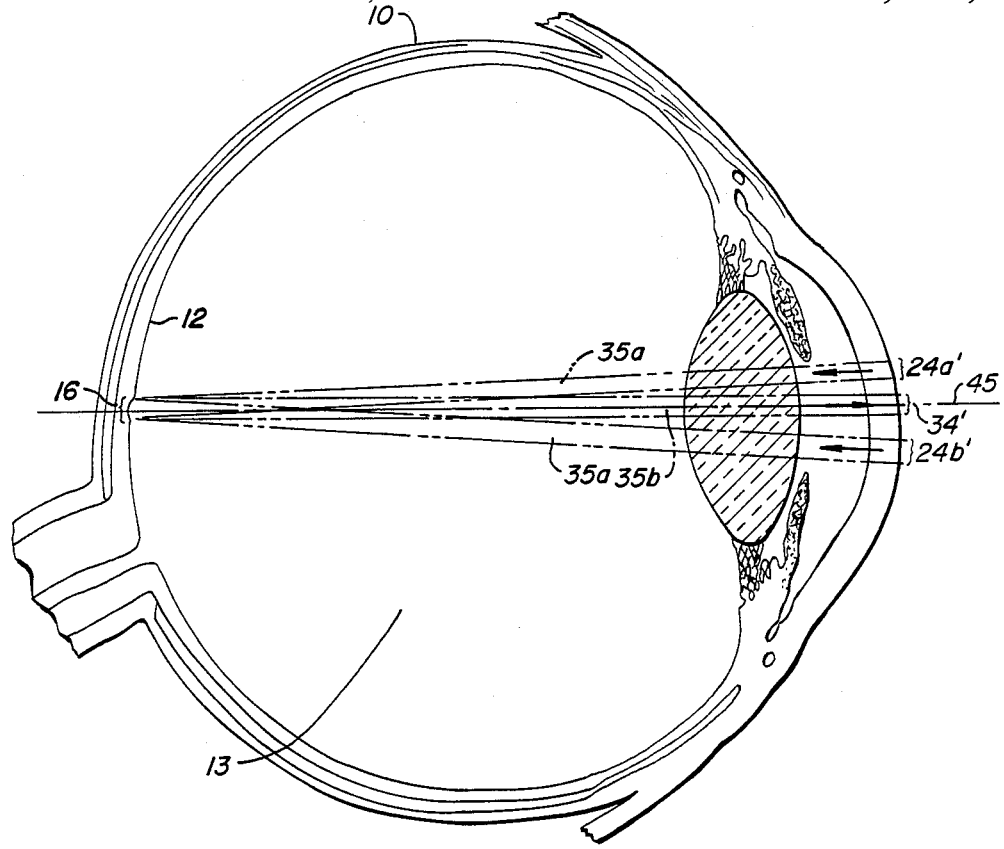
FIG._2.
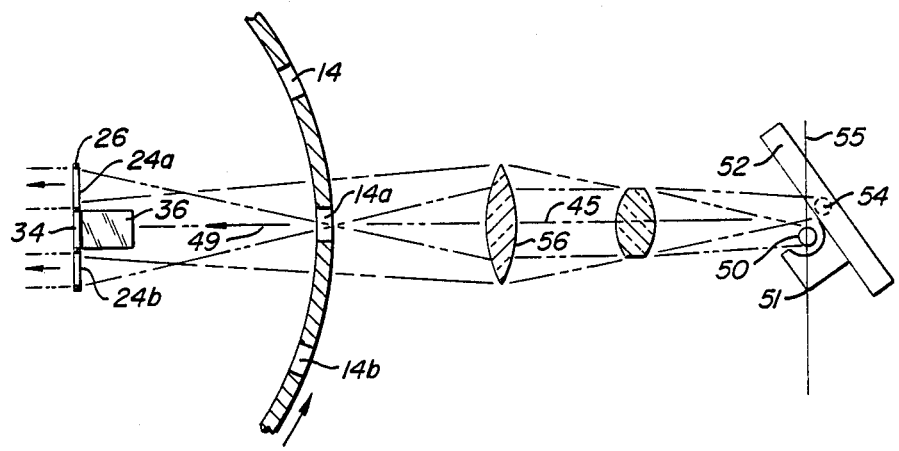
FIG._3.

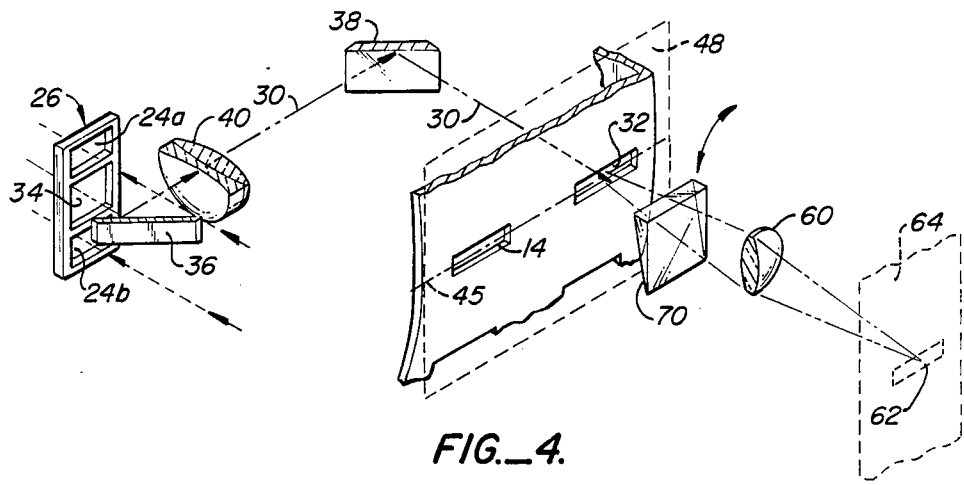
FIG._4.
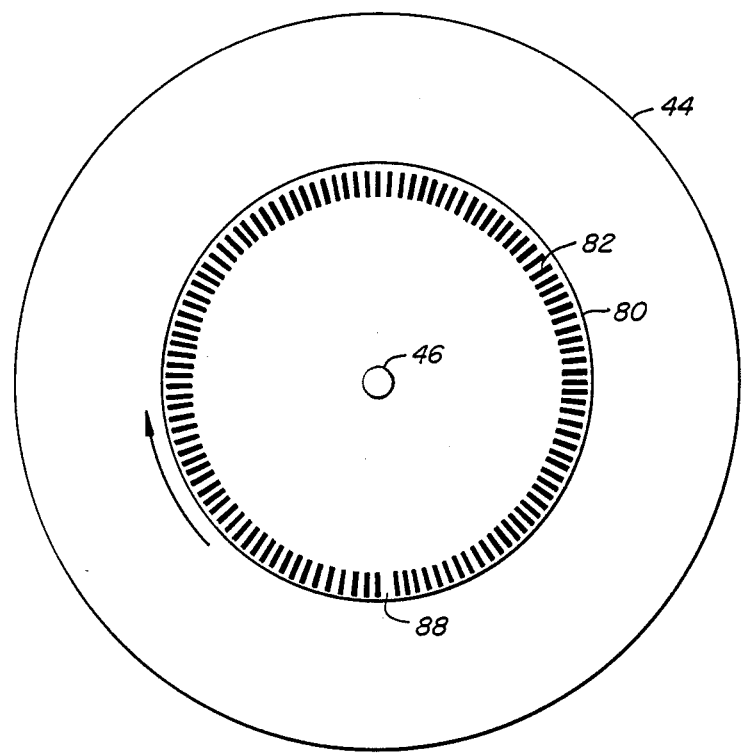
FIG._6.

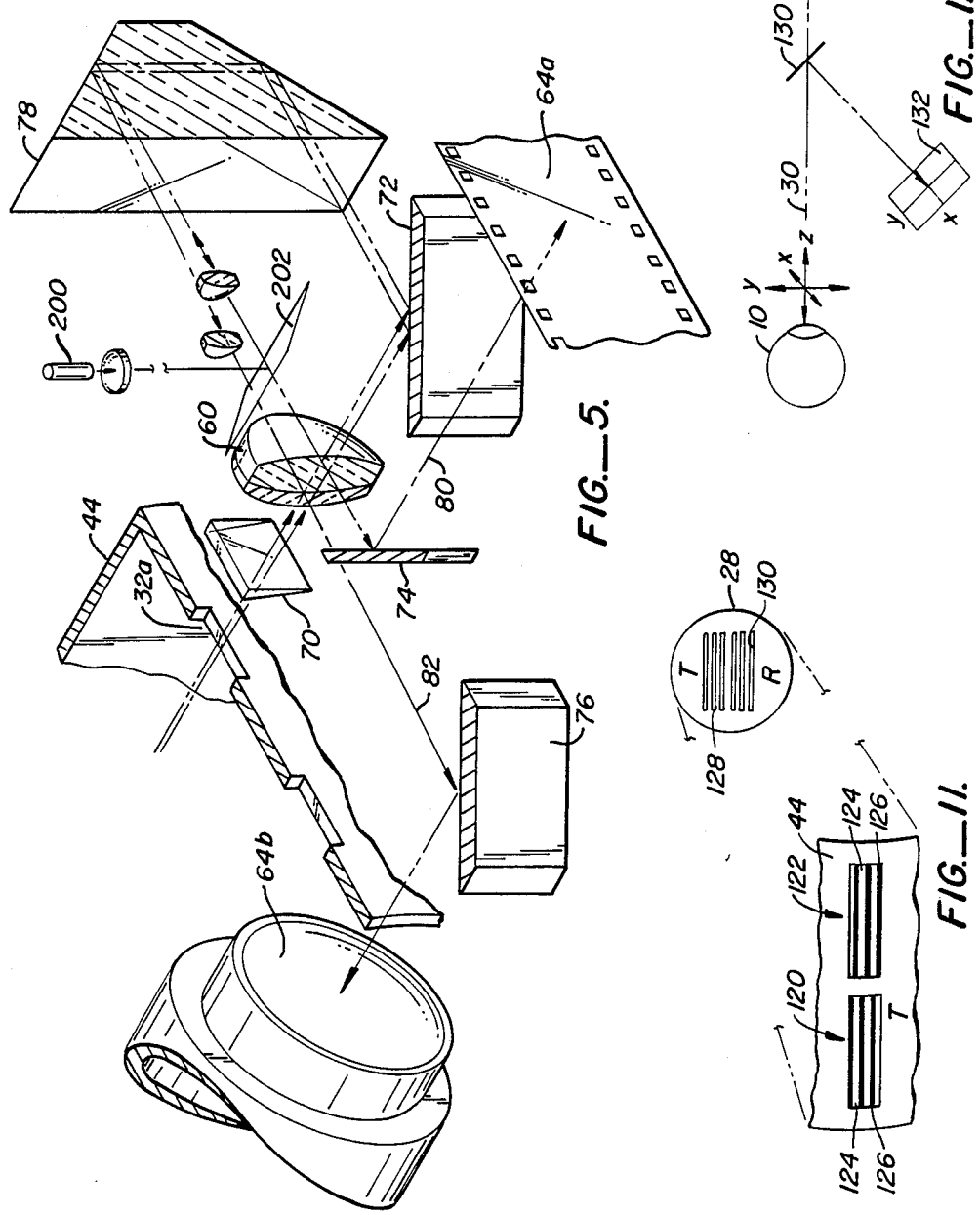

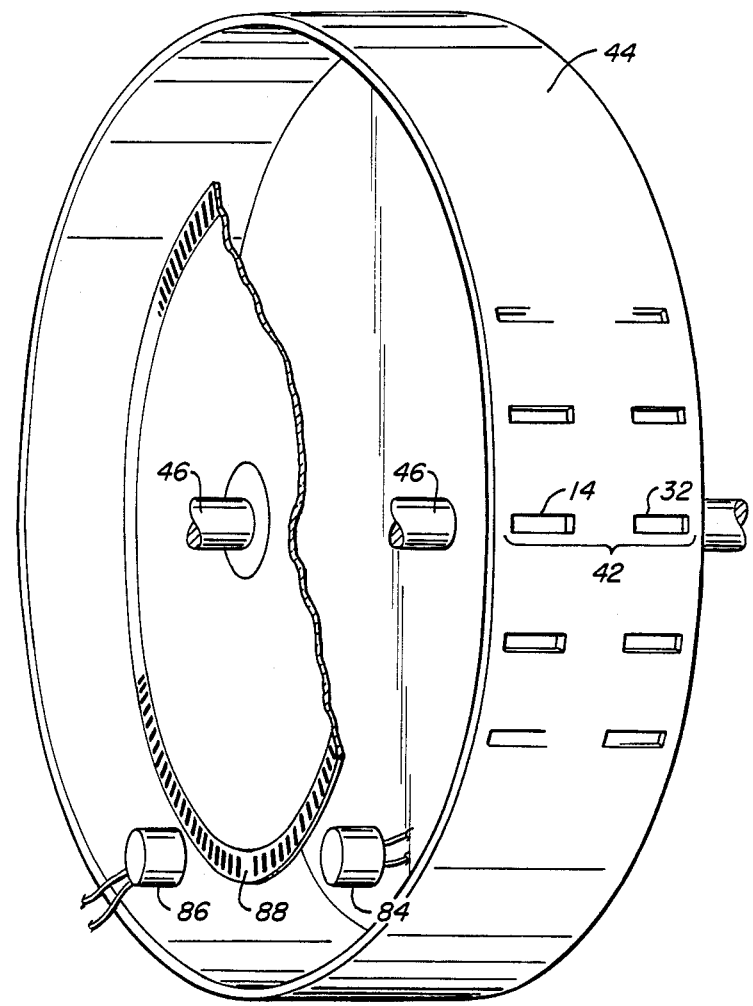
FIG._7.
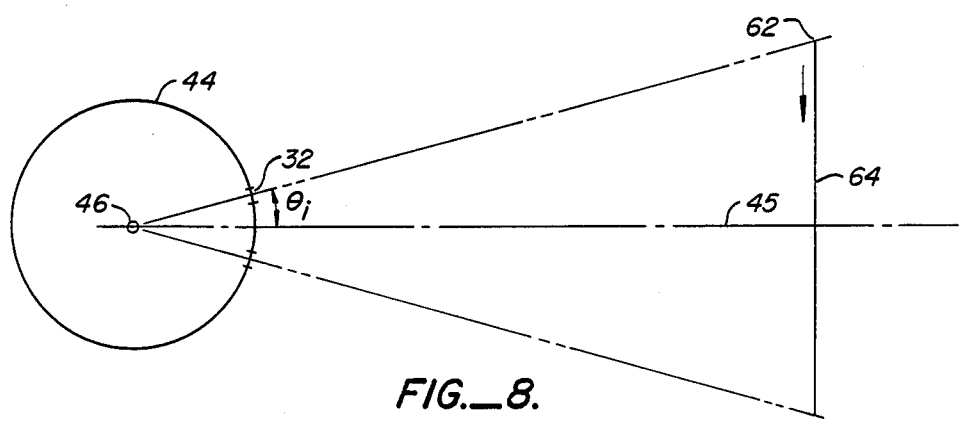
FIG._8.

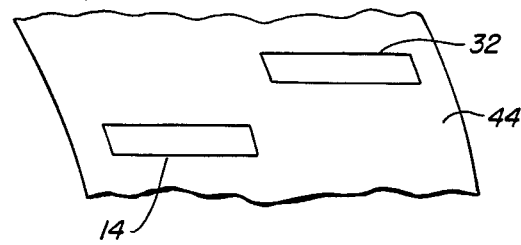
FIG._9.
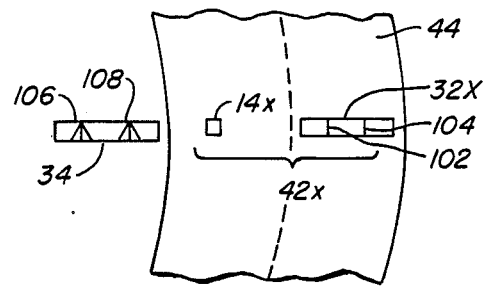
FIG._10A.
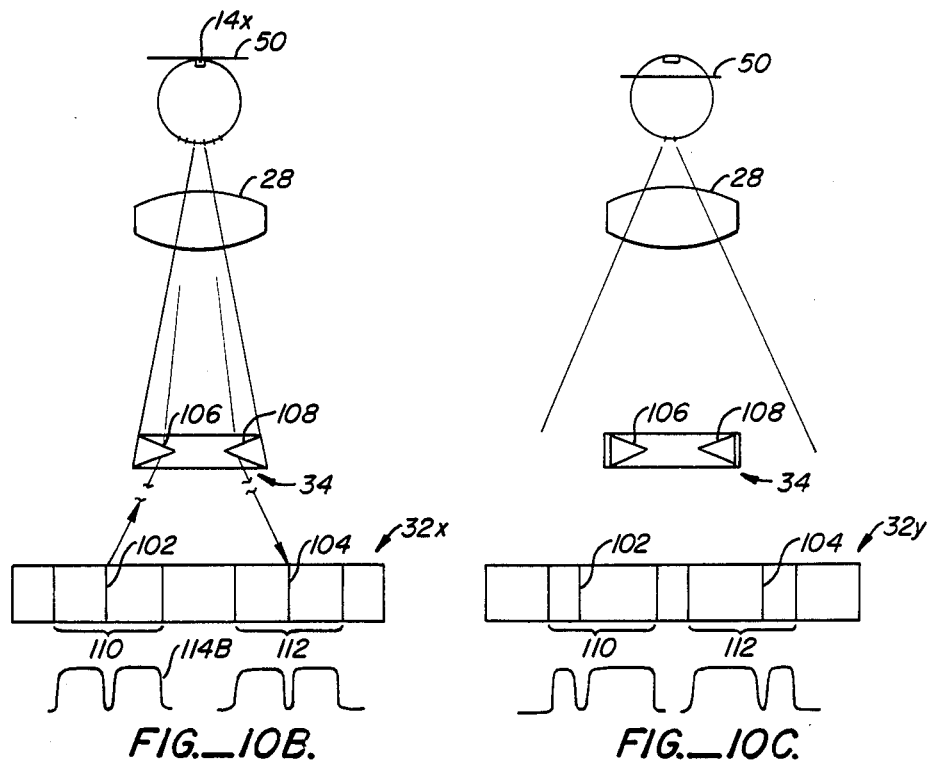
FIG._10B.   FIG._10C.

FUNDUS CAMERA

BACKGROUND OF THE INVENTION

1. Field of the Invention

The present invention relates generally to optical imaging systems and more particularly to an optical imaging system for forming an image of an object plane within a sample medium.

2. Description of the Prior Art

Generally, optical imaging systems form an image of the surface of an object. There is, however, an increasing need, especially within the medical arts, for optical systems that form high-quality images of a selected object plane within a sample medium. Generally, the sample medium is a human organ, such as, for example, the human eye. In the human eye the object plane may be selected to lie in the cornea or along the retina. High-quality images of the retina are vital to diagnosing a large variety of medical conditions.

The process of forming an optical image of an object plane includes the steps of illuminating the object plane, collecting the reflected light emanating from the object plane, and focusing the collected light on an image plane. Typically, these optical systems include lenses and mirrors to accomplish the various functions of illuminating, collecting, and focusing.

Forming a high-quality image of an object plane within a sample medium requires special techniques to overcome the deterioration of the image due to scattering of the illuminating light from the region of the sample medium external to the object plane. This scattered light is collected and focused along with light emanating from the object plane and thus obfuscates the image formed of the object plane.

Existing systems for imaging an object plane within a sample medium generally include an illuminating slit, for illuminating a region of the object plane, a viewing slit, for viewing the illuminated region of the object plane, and optics configured so that the region of the sample medium external to the object plane is not viewable through the viewing slit. Accordingly, most of the light scattered by the external sample medium will not pass through the viewing slit. Only the light passing through the viewing slit is focused on the image plane, thus, the obfuscation of the image of the object plane by this scattered light is substantially obviated.

The above-described systems only provide an image of a narrow, slit-shaped region of the object plane at a given time. To view a significant region of the object plane the slit is scanned across the object plane. Two examples of the above-described system are disclosed in U.S. Pat. Nos. 3,547,512 and 4,170,398 issued to Baer and Koester, respectively. In Baer, the illuminating slit and viewing slit are formed in planar diaphragms disposed substantially at right angles to each other. The scanning of the slits is accomplished by oscillating the diaphragms about an axis. In Koester, the illuminating and viewing slits are formed in planar diaphragms disposed substantially parallel to each other. In Koester the scanning of the slit is accomplished by a system utilizing a rotating mirror.

In U.S. Pat. No. 4,135,791 issued to Govignon, an optical fiber arrangement is utilized to scan an illumination beam along the retina and the illumination beam is synchronously viewed through a slit in a rotating diaphragm.

The above-described systems provide a high-quality image of an object plane in a sample medium such as, for example, the retina of the human eye. However, these devices do not provide for selectable alternate functions such as illuminating and viewing through colored filters to perform chemical analysis, non-coincident illumination and viewing, and stereo image formation. These functions are vitally important in many applications. Additionally, functions such as flare control, auto-focusing, and eye position error indication are highly desirable.

SUMMARY OF THE INVENTION

The present invention is a unique system for forming an image of an object plane in a sample medium, such as for example, the retina of the human eye.

In the present invention transmission and receiving slits are formed in a cylindrical drum. The long edges of the slits are disposed along a common axis parallel to the axis of the cylindrical drum.

The light passing through the transmission slit is guided along a transmission path formed by optical components including mirrors and lenses. The transmission path forms an image of the transmission slit on the object plane in the sample medium, where this image is denoted the illumination region. Thus the slit plane, i.e. the plane in which the transmission and receiving slits are located, and the object plane are conjugate planes. Correspondingly, a portion of the light emanating from the illumination region is guided to the receiving slit by optical elements in the receiving path. In the following discussion the light passing through the transmission slit that is focused onto the illumination region by the transmission path is termed the illumination beam and the light that is directed through the receiving slit by the receiving path is termed the viewing beam.

The illumination region is scanned across the object plane when the drum is rotated about its axis. The rate with which the illumination region scans the object plane is determined by the rate of rotation of the cylindrical drum. Scanning the illumination region across the object plane corresponds to the synchronous scanning of the illumination and viewing beams across the object plane.

In a preferred embodiment, the cylindrical drum has several transmission/receiving slit pairs formed thereon. Active optical elements, such as prisms, filters, lenses, or gratings, may be placed in a given slit pair so that slit performs a desired optical function. Additionally, in a given slit pair, the receiving slit may be displaced along the drum to provide for non-coincident illumination and viewing of the object plane. A system for selecting a specific slit function is also part of the invention.

Examples of slit function include full color photographic imagery, use of color filters for enhancing various retinal features, imagery using indirect illumination, and fluorescein angiography.

A further aspect of the invention is a system for determining the horizontal, vertical, and axial displacement of the eye from its correct position relative to the imaging system.

The transmission and receiving beams in the sample medium are optically displaced so that regions of the sample medium external to the object plane and illuminated by the illumination beam may not be viewed through the receiving slit, thereby preventing light scattered from the external sample medium from passing through the receiving slit and obfuscating the image of the object plane.

In one embodiment of the invention, the displacement of the transmission and receiving beams is accomplished by an aperture structure, including three apertures placed vertically with respect to the receiving path and a first receiving mirror positioned with its reflecting surface disposed to reflect light, emanating from the object plane and passing through the center aperture, along the receiving path; and with its non-reflective side disposed to block the illumination beam from passing through the center aperture of the aperture structure. This configuration results in a viewing beam positioned between two outer illumination beams where both illumination beams are focused on the illumination slit on the object plane.

According to a further aspect of the invention, a light source is provided for forming an input light beam incident on the transmission slit. This light source includes a flash lamp, a mirror for producing a flash lamp image, and a lamp lens for focusing the lamp and the lamp image on the first and second outer apertures of the aperture structure, respectively.

According to a still further aspect of the invention, an imaging path comprising mirrors and lenses directs the received light passing through said receiving slit (the output beam) to an image plane and focuses this light onto an image slit where the image slit is the optical image of said receiving slit, and where the slit plane and the image plane are conjugate planes.

According to a still further aspect of the invention, optical means are provided for directing the received light passing through said receiving beams to alternate imaging planes. Further, an electronic imaging device, for example a vidicon tube, may be utilized to receive this scanning imaging slit and produce an image of the object plane.

In one embodiment of the invention, the sweep of the vidicon tube is synchronized to the sweep of the imaging slit to thereby enhance the quality of the vidicon tube image and to provide for reception of successively scanned illumination slits having a short time interval therebetween.

In another embodiment, an autofocusing feature is included. Prisms are placed in the center aperture to deflect the image of the transmission slit and the position of wires, disposed in the receiving slit, relative to the deflected images is utilized to determine whether the system is in focus.

The ability of the present system to provide multiple slit functions provides for hitherto unavailable optical images of the eye. Different color filters may be placed in the transmission and receiving slits to highlight retinal features. Illumination and viewing may be performed through displaced slits for imaging using indirect illumination. Additionally the present invention provides many other advantages not realized in the art.

BRIEF DESCRIPTION OF THE DRAWINGS

FIG. 1 is a stylized perspective view depicting the various components of a preferred embodiment of the invention.

FIG. 2 is an expanded view of the eye showing the positions of the illuminating and viewing beams.

FIG. 3 is a schematic diagram depicting the optical components utilized to provide an input light beam to the system.

FIG. 4 depicts the image plane.

FIG. 5 is a schematic diagram of the optical components utilized to selectively direct the output beam from the receiving slit to alternate image planes.

FIG. 6 is a side view of the cylindrical drum.

FIG. 7 is a perspective view of the cylindrical drum.

FIG. 8 is a schematic diagram illustrating the scanning of a vidicon.

FIG. 9 is a view of a slit pair having displaced slits.

FIG. 10 is a perspective view of the drum and center aperture.

FIG. 11 is a perspective view of the drum and eye lens.

FIG. 12 is a perspective view of the eye position error detection system.

DETAILED DESCRIPTION OF THE PREFERRED EMBODIMENTS

The present invention is a novel system for forming an image of an object plane disposed in a sample medium.

FIG. 1 is a highly stylized view, in perspective, of a section of the present invention. In FIG. 1, by way of example and not limitation, the sample medium is a human eye 10 with the object plane being the retina, or fundus, 12 of the eye. The interior of the eye 13 scatters the incoming light utilized to form an image of the retina 12. Incoming light transmitted through a transmission slit 14, termed the illumination beam, is directed to an illumination region 16 on the retina 12 by a transmission path 17 comprising first and second transmission mirrors 18 and 20, a transmission aperture lens 22, a first and second outer apertures 24a and 24b of an aperture structure 26, and an objective 28. A portion of the light emanating from the illumination region 16, termed the viewing beam, is directed along a receiving path 30 through a receiving slit 32 by the optical elements in the receiving path 30. The receiving path comprises the eye lens 28, the center aperture 34 of the aperture structure 26, first and second receiving mirrors 36 and 38 and a receiving aperture lens 40.

The first receiving mirror 36 is positioned so that only light passing through the center aperture 34 is reflected into the receiving path 30. Thus, light emanating from the illumination region 16 that passes through the first and second outer apertures 24a and 24b is not directed through the receivng slit 32. The non-reflective surface of the first receiving mirror 36 prevents light in the illumination beam from passing through the center aperture 34. Thus, the transmission beam passes through only the first and second outer apertures 24a and 24b and not through the center aperture 34.

FIG. 2 is a more detailed view of the human eye 10 showing the configuration of the illumination and viewing beams 35a and b. Referring to FIG. 2, the optics of the system are designed to focus 24a', 24b' and 34' images of the outer and center apertures 24a, 24b, and 34 on the pupil of the eye 10. The illumination beam 35a is formed only from light passing through the outer aperture images 24a' and b' because the nonreflecting surface of the first receiving mirror 36 in FIG. 1. prevents passage of light through the center aperture 34 to the eye 10. This light is focused onto the illumination region 16 as described above.

Correspondingly, only the light emanating from the object plane that passes through the center aperture image 34' is reflected by the reflective surface of the first receiving mirror 36 along the receiving path 30 and through the receiving slit 32.

Only the region of the interior of the eye included in the illumination beam 35a is illuminated by light passing through the transmission slit 14. Similarly, only the region of the interior of the eye included in the viewing beam 35b is viewable through the receiving slit 32.

The interaction of the aperture structure 24, as the first receiving mirror 36, and the other elements of the transmission and receiving paths 17 and 30 cause the illumination and viewing beams 35a and b to be angularly displaced within the interior eye. Because of this angular displacement, much of the illuminated region of the interior of the eye external to the retina 12 is not viewable through the receiving slit 32. Thus, most of the light scattered from the illuminated interior of the eye external to the retina 12 does not pass through the receiving slit 32 to obfuscate the image of the retina 12.

Referring back to FIG. 1 the transmission/receiving slit pair 42 is formed in a diaphragm in the shape of a cylindrical drum 44. The cylindrical drum 44 is depicted in greater detail in FIG. 7. The cylindrical drum has an axis of symmetry 46 about which the drum is rotated to scan the illumination slit across the retina 16. The drum includes a plurality of transmission/receiving slit pairs 42 displaced circumferentially around the drum 44. Eye lens 28 is selected so that the apertures 24a, 24b and 36 are focused on the pupil of the eye 10, and so that the plane of the pupil and the plane of the aperture structure 26 are conjugate planes. Additionally, the system is configured so that the transmission slit 14 and receiving slit 32 are imaged at the illumination region 16 on the retina.

A start configuration will now be described where the transmission/receiving slit pair 42, receiving mirrors 36 and 38, transmission mirrors 18 and 20, aperture lenses 22 and 40, eye lens 28, and drum axis 46 are all in the same plane designated the axis plane 45. A slit plane 48 is defined as the plane perpendicular to the axis plane 45 having the transmission/receiving slit pair 42 disposed thereon when in the start configuration, while the object plane 50 is the plane perpendicular to the axis plane having the illumination region 16 disposed thereon when in the start position. All points disposed on the slit plane 48 will be imaged on the object plane 50 by the optical system, thus, the slit plane 48 and object plane 50 are termed conjugate planes. As the drum 44 is rotated, the transmission/receiving slit pair 42 are displaced along the slit plane 48 while the illumination region 16 is displaced along the object plane 50. Thus, the object plane 50 can be scanned by the illumination region 16 if the drum 44 is rotated. Obviously, as the drum is rotated the slit pair 42 is displaced from the slit plane 48 due to the circular shape of the drum 44. A good image of the slits 14 and 32 is maintained on the retina 12 within a critical angular displacement from the axis plane 45.

The path length of the transmission and receiving beams 17 and 30 must be equal for the beams to scan the retina at the same rate. A unique Z configuration in the transmission path 17 formed by the placement of transmission mirrors 18 and 20 equalizes the path length of the transmission path and receiving path 17 and 30.

FIG. 3 is a side view taken perpendicularly to the axis plane 45 depicting a unique source configuration for providing input light to the illumination beam 35a. A flash lamp 50 and reflector 51 are disposed slightly below the axis plane 45. A source mirror 52 is utilized to create a source image 54 of the flash lamp 50 where the flash lamp 50 and the source image are symmetrically disposed about the axis plane 45 and are positioned in a source plane 55 disposed almost perpendicularly to the axis plane 45 (see FIG. 3). Source lens 56 is positioned between the transmission slit 14 and the source plane 55. The source lens 56 has its optical axis disposed in the start plane 45 and is configured so that images of the flash lamp 50 and the source image 54 are focused at the first and second outer apertures 24a and 24b, respectively, of the aperture structure 26. This configuration assures that most of the light generated from the flash lamp 50 passes through the first and second outer apertures along the transmission path 17. Note that as the drum 44 rotates, the first transmission slit 14a will eventually reach an angle after which light from the source will no longer pass through the transmission slit and through the first and second outer apertures 24a and 24b. This angle determines the outer limits of the angular sweep of the illumination slit along the retina of the eye. No light from the source will traverse the transmission path to the illumination slit until a subsequent transmission slit 14b enters the critical angular range. The duration of the flash produced by the flash lamp is timed so that the scanning transmission slit is illuminated throughout the entire critical angular range. The flash then recycles in time to illuminate the successive transmission slit when it is in the critical angular range. In practice, there is about a 1/30th of a second time period between the appearances of successive transmission slits 14 in the start plane 39.

FIG. 3 also illustrates how the placement of the first receiving mirror 36 prevents light in the illumination beam from passing through the center aperture 34 of the aperture structure 26. The non-reflective side of the first receiving mirror 36 is positioned to block outgoing light from passing through the center aperture 34.

FIG. 4 is a schematic diagram of an imaging path utilized to direct light passing through the receiving slit 32 onto an image region 62 formed on an image plane 64. An imaging lens 60 forms an image of the receiving slit 32 on an image plane 64. Thus, light from the illumination region 14 passing through the receiving slit 32 will be focused into the image region 62 which is the image of the receiving slit 32. The image plane 64 is conjugate to the slit plane 48 and, since the slit plane 48 is conjugate to the object plane 50, the image plane 64 and object plane 50 are also conjugate planes. The vertical displacement of the receiving slit 32 due to the rotation of the drum 44 causes the image region 62 to sweep across the image plane 64, thus forming an image of the region of the object plane 50 being swept by the illumination region 16. The light passing through the receiving slit 32 that is focussed onto image plane 64 by the image path is termed the output beam.

FIG. 4 also illustrates how the receiving mirror 36 only directs incoming light passing through the center aperture 34 of the aperture structure 26 into the receiving beam 30. Note that incoming light passes through all the apertures 24a, 24b, and 34, however, the receiving mirror 36 is positioned so that only incoming light passing through the center aperture 34 is deflected into the receiving path 30.

Any suitable medium for storing the image of the retina formed on the image plane 64 may be utilized. For example, photographic film may be placed at the image plane 64 and the sweep of the imaging slit 62 across the planar surface of the film is analogous to the sweep of a focal plane shutter across the film.

Of particular advantage in the present invention is the use of a vidicon tube to record the image formed by the illumination slit sweeping across the illumination plane 62. A vidicon tube includes a light receiving surface which is swept by an electron beam. This sweeping of the electron beam is accomplished by sequential horizontal sweeps of the beam where the beam is stepped vertically at the completion of each horizontal sweep. The electron beam is part of a circuit that includes the light receiving surface of the vidicon tube, where the conductivity of the vidicon tube is determined by the magnitude of light intensity at the point of impact of the electron beam on the light receiving surface. Thus, the intensity of the light at a given point is measured by the amount of electron current generated when the electron beam is incident at that point.

In one embodiment of the present invention, the light receiving surface of the vidicon tube is positioned to be coincident with the imaging plane 64. The image formed by the vidicon tube is greatly enhanced if the vertical stepping of the sweep of the electron beam across the light receiving surface of the vidicon tube is synchronized with the sweep of the imaging slit 62 across the light receiving surface of the vidicon tube. This synchronization is accomplished in the present invention by a synchronization mechanism which will be described below.

FIG. 5 depicts an arrangement for selectively directing the output from a transmission slit 32 to either a first or a second image plane 64a or b. Referring now to FIG. 5, a prism 70 is removably mounted between drum and lens 60. The prism deflects the output beam from the receiving slit 32a and in conjunction with first, second, and third imaging mirrors 72, 74, 76, and a fixed prism 78 forms two alternate image paths depending upon whether or not the first prism 70 is in receiving path. If the first prism 70 is in place, then the output beam follows the first image path 80 and is reflected from second imaging mirror 74 onto the first image plane 64a; while if the small prism 70 is not in place, the output beam follows a second image path 82 and is reflected from the third image mirror 76 to the second image plane 64b. As shown in the figure, photographic film may be placed at the first image plane 64a while the vidicon light receiving surface may be placed at the second image plane 64a.

Turning now to FIGS. 6-8, the system for synchronizing the sweep of the imaging slit and the electron beam across the light receiving surface of the vidicon tube will now be described.

As described above, with reference to FIG. 4, when the transmission slit 32 is positioned in the axis plane 45 the imaging slit 62 is positioned in the start position on the image plane 64. As the transmission slit 32 is angularly displaced from the start plane 39 the imaging slit 62 is displaced along the image plane 64 a corresponding distance from the start position.

Referring now to FIG. 6, the rotating drum 44 includes a mechanism for indicating the angular displacement of each receiving slit 32 from the start plane 39. This mechanism includes a transparent ring 80 with a set of opaque notches 82 equally spaced about the ring 80. This transparent ring 80 is positioned in the base of the drum 44 with the center of the ring positioned at the axis 46 of the drum 44.

Referring now to FIG. 7, a mechanism for utilizing the transparent ring/opaque notch arrangement 80/82 is illustrated. A light source 84 and detector 86 are disposed on opposite sides of the transparent ring 80. The detector 86 produces a signal indicating the intensity of the light received at its surface. When an opaque notch 80 is positioned between the light source 84 and detector 86 the intensity of the detector signal decreases. The output from the detector 86 is connected to an electronic position counter (not shown) that counts the number of times the output signal from the detector 86 decreases in response to the appearance of an opaque notch 80 between the detector 86 and the light source 84. An arbitrary reference point 88 is provided in the transparent ring/opaque notch arrangement 80/82 that resets the position counter whenever the reference point 88 appears between the detector 86 and the light source 84. In the embodiment depicted in FIG. 7, the reference point 88 comprises an omitted notch where the lack of a regularly timed decrease in the detector output signal indicates to the associated electronic circuitry that the position counter is to be reset. In the embodiment depicted, 256 opaque notches 82 are equally positioned about the circular ring 80. Thus, the angular position of the drum relative to the reference point 88 may be determined to an accuracy of 1 part in 256. In practice, the light source 84 and detector 86 are positioned so that the counter is set to zero when the reference mark 88 passes through the axis plane 45.

The location of each transmission/receiving slit pair 42 along the circumference of the drum 44 corresponds to a specified output of the position counter. The utilization of the position counter output to synchronize the sweep of the imaging slit 62 to the vertical stepping electron beam sweep across the light receiving surface of the vidicon tube will now be described with reference to FIG. 8. In FIG. 8, the image region 62 is positioned at an initial position on the light receiving surface of the vidicon tube 64, which, in FIG. 8, corresponds to the top of the light receiving surface, when the receiving slit 32 is displaced from the axis plane 45 by an initial angle $\theta_i$. This angle $\theta_i$ corresponds to a specific number of counts, $C_i$, in the position counter. This specific number, $C_i$, is stored in a synchronization register (not shown) and is continually compared with the output of the position counter. When the output of the position counter is equal to $C_i$ the sweep of the electron beam across the light receiving surface of the vidicon tube is initiated.

The sweep of the image region 62 and the vertical stepping of the electron beam across the light receiving surface of the vidicon tube 64 is synchronized by controlling the rate of rotation of the drum 44 so that the light receiving surface 64 is vertically swept by th image region slit 62 and the electron beam at the same rate.

The sweep of the electron beam in the vidicon tube may be synchronized to any selected number of transmission slits 32 by storing the angle counter outputs corresponding to the initial angle for each successive slit 32 in memory and initiating a sweep of the electron beam whenever the output from the angle counter matches one of the preselected angle counter outputs stored in memory.

Of particular advantage to the present invention is the capability of placing active optical elements in selected transmission/slit pairs so that the selected slit pair performs a desired optical function.

Other examples include the placement of colored filters in the slits of a selected transmission/receiving slit pair 42 to highlight certain features of the retina image.

FIG. 9 illustrates a displaced slit function where a viewing region is scanned across the retina a predetermined delay time after the illumination region is scanned.

The mechanism described above with reference to FIGS. 6 and 7 is utilized to select a specific function. The number of counts, $C_i$, indicating that the slit configured to perform the selected function is in position, is stored in the synchronization register. When $C_i$ appears in the position register the image is formed.

An auto focusing system for use with the present invention will now be described with reference to FIGS. 10A-10C. In FIG. 10A, a transmission/reception slit pair 42x includes transmission slit 14x in the shape of a small square and receiving slit 32x including a pair of vertical wires 102 and 104. A pair of focus prisms 106 and 108 are positioned in the center aperture 34 of the aperture structure 26.

Referring now to FIG. 10B, a top view of the axis plane 45 depicts the operation of the autofocus system when the image of the square transmission slit 14x is in focus, i.e., the image of slit 42x at the retina 12 is at the object plane 50. The focusing prisms 106 and 108 deflect the image of the square transmission slit 14x to form two focusing images 110 and 112 at the receiving slit 32x. The wires 102 and 104 are positioned to be in the center of the focusing images 112 and 114. The output of the vidicon tube for this configuration is depicted in graphs 114B and 116B.

In FIG. 10B, the system is depicted where the image of slit 42x at retina is out of focus, e.g., the retina is behind the object plane 50. The images 110 and 112 of the square transmission slit 14x are horizontally displaced so that the wires 102 and 104 are no longer centered. The corresponding vidicon outputs are illustrated in graphs 114C and 116C.

The vidicon output signals can be utilized as part of a feedback system to adjust the optics of the system to center the wires 102 and 104 thereby providing an autofocus capability to the system.

FIG. 11 illustrates that a unique system of flare control may also be implemented in the pesent invention. Referring first back to FIG. 1, reflection of the illumination beam 17 from the surface of the eye lens 28 causes a bright spot to form on the image. Referring now to FIG. 11, a transmission slit 14 and receiving slit 32 have transmission and receiving grids 120 and 122 placed to intercept the illumination beam and viewing beam, respectively. Note that each grid has a pattern including open and closed areas 124 and 126. The patterns are designed so that if the grids 120 and 122 were overlaid, the closed areas 126 of the receiving grid 122 would overlay the open area 124 of the transmission grid 120.

The grids 120 and 122 are mounted to be displaced from the slits 14 and 32 in the direction toward the eye lens 28 and imaged at eye lens. The images 128 and 130 of the transmission and receiving grids 120 and 122 on the surface of the eye lens 28 are shown displaced vertically to better explain the invention. In practice these images 128 and 130 would overlap and the closed areas 126 of receiving grid image 130 would cover the open areas 124 of the transmission grid image 128. These open areas 124 are the illuminated regions of the surface of the eye lens 28. Thus, the closed areas 126 of the receiving grid block these illuminated regions from view through the receiving slit 32 and prevent flare of the eye lens 28 from appearing on the image.

It is important that the camera be positioned in the correct distance from the eye in order to achieve optimum focus. This is done by a simplified automated system that can be understood with reference to FIG. 5. Referring to FIG. 5, a small light emitting diode 200 is imaged through the receiving system via a beam splitter 202. This image is reflected by the eye and focused on the quad detector.

The operation of the system can be understood by analyzing three cases. First, if the eye is in the correct position and the slit scanning camera scans past the infrared image in the eye, there will be no relative movement of the image during the scan at the detector as the image will be properly focused at the detector. As there is no relative movement, this will flag that the eye is correctly spaced from the camera.

Assuming that the eye is too close, there will be relative movement of the image as the image will be out of focus at the detector. This relative movement will have both magnitude and sign. The movement of the image across the detector segments will be, for example, from positive x to negative x as illustrated in FIG. 12.

Finally, if the eye is too far away, the magnitude will indicate the distance and the direction of movement will be opposite on the quad detector 132 as illustrated in FIG. 12. The out of focus of the image at the detector will be beyond optimum focus; relative image movement will thus be opposite.

Referring to FIG. 12 it can be seen that centering of the eye in the x and y planes is straightforward.

The above description of the invention is illustrative only and does limit its scope. For example, in applications where active optical elements are not required in the receiving slit, a drum having only transmission slits may be utilized. Additionally, different lens configurations other than the ones illustrated may be utilized to achieve the same effects. Alternative means for determining drum positioning and performing slit selection are within the skill of the art. Additionally, although a flash lamp has been described as the light source, a constant light source with a timed shutter mechanism could be substituted to perform the function selection features described above. Accordingly, the scope of the invention is determined by the appended claims.

What is claimed is:

1. An improvement in a fundus camera for forming an image of a fundus of the eye through the cornea of the eye, comprising: a transmission path for guiding and focusing an illumination beam onto an illuminated region of the fundus; a receiving path for viewing the illuminated region of the fundus where the transmission path and the receiving path are substantially separate so that the transmission path of light to the fundus is substantially excluded from the receiving path of light from the fundus thereby preventing light scattered by the illuminated region of the eye to the fundus from obfuscating the image of the fundus, a cylindrical drum formed about a drum axis having a transmission slit and a receiving slit parallel to the axis of said drum slit, the transmission slit being formed in a first cylindrical segment of said drum and the receiving slit being formed in a second cylindrical segment of said drum;

means for routing the transmission path to the first cylindrical segment of the cylindrical drum having the transmission slit;

a transmission aperture between the cylindrical drum and the eye;

means for relaying a conjugate image of the transmission aperture to the cornea of the eye in at least one first discrete zone;

means for routing the receiving path to the second cylindrical segment of the cylindrical drum having the receiving slit;

a receiving aperture between the drum and the eye;

means for relaying a conjugate image of the receiving aperture to the cornea of the eye in at least a second discrete zone separate from the first discrete zone;

means for focusing the image of the transmission slit and the receiving slit on the fundus of the eye as the transmission and receiving slits move into and through said respective transmission path and the receiving path;

means for rotating the cylindrical drum about the drum axis to scan across the fundus whereby focused images of the transmission slit and the receiving slit pass across the fundus of the eye from the first discrete zone and second discrete zone without substantial overlap of the transmission path and the receiving path.

2. A fundus camera for producing an image of a fundus disposed within an eye through the cornea of the eye comprising:

a cylindrical drum formed about a central axis;

a first pair of rectangular slits, including a transmission slit and receiving slit, formed in the cylindrical drum with the rectangular slits disposed parallel to the central axis of the cylindrical drum;

means for focusing the images of the respective transmission slit and receiving slit through a respective light transmission path and a light receiving path on the fundus, thereby causing said transmission and receiving slits and the fundus to be conjugate, at least a first pair of apertures including a transmission aperture and a receiving aperture, the first positioned between the cylindrical drum and the eye, the transmission aperture being positioned in the light transmission path and the receiving aperture in the light receiving path;

means for focusing on the cornea of the eye a conjugate image of the transmission aperture and the receiving aperture at discrete and different zones on said eye;

an illumination beam;

means for directing an illumination beam transmitted through the transmission slit along the transmission path, into a first illumination region formed on the fundus where the first illumination region is the image of the transmission slit;

means for positioning the image of the receiving slit on the fundus to be substantially coincident with the first illumination region and for returning a viewing beam, along the light receiving path and through the receiving slit;

means for angularly displacing the viewing beam from the illumination beam when said beams are within the eye to the fundus; and, means of rotating the cylindrical drum about the central axis of the drum.

3. The invention of claim 2 wherein said means for angularly displacing said viewing beam from said illumination beam comprises:

an aperture structure defining a center receiving aperture and first and second outer transmission apertures positioned above and below said center aperture, the aperture structure disposed in front of the eye; and a first receiving mirror with its non-reflective side positioned to block light transmitted through said transmission slit from passing through said center receiving aperture and with its reflective side positioned to direct light emanating from the first illumination region through the center aperture, along the receiving path.

4. The invention of claim 3 further comprising:

means for focusing the light received through the receiving slit into an image region formed on an image plane, where the image region is the image of the receiving slit and wherein the fundus, the transmission and receiving slits, and image plane are all conjugate planes.

5. The invention of claim 4 wherein said transmission illumination beam comprises:

a light source;

a source mirror for forming an image of the light source;

first and second transmission mirrors aligned to direct light from the light source and the image of the light source to the aperture structure where the light from said source and source image travels along a source/aperture structure light path; and a source lens positioned in said source/aperture structure light path for focusing the light source and the light source image onto the first and second outer transmission apertures respectively.

6. The invention of claim 11 wherein said light receiving path comprises:

a second receiving mirror for directing light reflected from said first receiving mirror through said receiving slit; and a receiving aperture lens positioned between said first and second receiving mirrors.

7. The invention of claim 6 wherein said first and second transmission mirrors, said first and second receiving mirrors, said center aperture, and said drum axis are disposed about a common axis plane.

8. The invention of claim 7 wherein said means for scanning the images of said transmission and receiving sits at the same rate comprises:

said first and second transmission mirrors disposing said transmission light path in a first Z configuration and said receiving light path in a second Z configuration for equalizing the lengths of said light transmission and said light receiving paths.

9. The invention of claim 8 further comprising:

first and second imaging planes; and means for selectively directing the light transmitted through said receiving slit to either said first or said second image plane.

10. An improvement in a fundus camera for forming an image of the fundus disposed in an eye, said fundus camera comprising: a transmission path for guiding and focusing an illumination beam onto an illumination region of the fundus:

a receiving path for viewing the illuminated region of the fundus where the transmission and receiving paths are configured so that the illuminated region of the eye external to the fundus is not substantially included in the receiving path thereby preventing light scattered by the illuminated region of the eye to the fundus from obfuscating the image of the fundus;

a cylindrical drum having a transmission/receiving slit pair, each of the transmission/receiving slit pair rectilinear and aligned parallel to the axis of said cylinder;

optical means for forming a conjugate of the fundus at a surface of said cylindrical drum to enable images of the transmission/receiving slit pair to pass across the fundus of the eye;

means for rotating the cylindrical drum to scan the images of the transmission/receiving slit across the fundus; and optical means, disposed in the transmission/receiving slit pair, for performing a selected function; said optical means selected from a group consisting of prisms, filters, lenses, gratings and reticles.

11. An improvement in a fundus camera for forming an image of a fundus disposed in an eye, said system comprising: a transmission path for guiding and focusing an illumination beam onto an illuminated region of the fundus; a receiving path for viewing a viewing region of the fundus where the transmission and receiving paths are configured so that the illuminated region of the eye external to the fundus is not included in the receiving path thereby preventing light scattered by the illuminated region of the eye external to the fundus from obfuscating the image of the fundus;

a cylindrical drum formed about a central axis having a rectilinear transmission slit and a rectilinear receiving slit formed thereto, said slits extending parallel to the axis of said cylindrical drum and being at differing angular intervals from the central axis of the cylindrical drum; and means for rotating the cylindrical drum about the central axis to scan the illuminated region and viewing region across the fundus whereby the images of the transmission and receiving slits are non-coincident at said fundus.

12. An improvement in a fundus camera for forming an image of a fundus disposed in an eye, said camera comprising:

a transmission path for guiding and focusing an illumination beam onto an illuminated region of the fundus;

a receiving path for viewing the illuminated region of the fundus where the transmission and receiving paths are configured so that the illuminated region of the eye external to the fundus is not substantially included in the receiving path thereby preventing light scattered by the illuminated region of the eye to the fundus from obfuscating the image of the fundus:

a rotating drum having a plurality of transmission/receiving slit pairs formed thereon with each of said transmission/receiving slit pairs rotating through the respective transmission and receiving paths, and where each of the transmission/receiving slit pairs is configured to perform a selected optical function; and optical means for forming an image of the transmission/receiving slit pairs on the fundus of the eye when the transmission/receiving slit pairs rotate through the transmission/receiving paths;

means for illuminating at least one of said transmission/receiving slit pairs at the transmission slit upon passage through said transmission path for forming an image of said fundus through a selected one of said plurality of transmission/receiving slit pairs.

13. An improvement in a fundus camera for forming an image of a fundus disposed in an eye, said camera comprising:

a transmission path for guiding and focusing an illumination beam onto an illuminated region of the fundus;

a receiving path for reviewing the illuminated region of the fundus along a viewing beam; where the transmission and receiving paths include a common lens for focusing said illumination beam and the illuminated region of the funds, and are configured so that the illuminated regio of the eye external to the fundus is not included in the receiving path thereby preventing light scattered by the illuminated region of the eye external to the fundus from obfuscating the image of the fundus:

a common lens disposed in both said transmission path and said receiving path;

a cylindrical drum formed about a central axis and having rectilinear transmission and receiving slits, defined in the side walls of said drum parallel to the axis of said drum, said walls of said drum included in said transmission and receiving paths respectively;

means for rotating said drum to scan the transmission and receiving slits across the fundus;

a transmission grid in the transmission slit, the transmission grid patterned with open and closed sections and disposed to intercept the illumination beam;

a receiving grid in the receiving slit, the receiving grid patterned with closed and open sections, disposed to intercept the viewing beam; and means for forming an image of the transmission and receiving grids at the common lens, with the grids positioned so that the image of the receiving grid at the common lens is displaced from the image of the transmission grid at the common lens so that the closed section of the transmission grid is coincidence with the open of the receiving grid and the closed section of the receiving grid is coincident with the open section of the transmission grid whereby light reflected from the common lens is rejected form the receiving path.

14. An improvement in a fundus camera for forming an image of a fundus disposed in an eye, the camera comprising:

a transmission path for guiding and focusing an illumination beam onto an illuminated region of the fundus;

a receiving path for viewing the illuminated region of the fundus where the transmission and receiving paths are configured so that the illuminated region of the eye external to the fundus is not substantially included in the receiving path thereby preventing light scattered by the illuminated region of the eye external to the fundus from obfuscating the image of the fundus:

a cylindrical drum having side walls formed about a central axis and defining a transmission/receiving paths respectively at the side walls of the cylinder;

means for forming conjugate images of said cylinder side walls at the transmission and receiving paths to the fundus of the eye;

means for rotating the cylindrical drum about the central axis to pass the transmission and receiving slits through the transmission and receiving paths whereby image of the transmission and receiving slits traverse the fundus;

a center aperture in one of said slits and a second aperture structure in the other of said slits including first and second outer apertures.

a pair of focusing prisms; disposed in the center receiving aperture, for horizontally deflecting the image of the illuminated region, with said focusing prisms adapted to deflect said image in opposite directions; and means for measuring the distance said image is deflected to determine whether the illuminated region is in focus.

15. The invention of claim 14 wherein said means for measuring comprises:

a vertical wire, disposed in the receiving slit, with said wire positioned to intersect one of the deflected images at a selected point of said image when said illuminated region is in focus; and means for determining the point at which said wire intersects said deflected image.

16. An improvement of a fundus camera for forming an image of the fundus of an eye, said camera comprising:

a transmission path for guiding and focusing an illumination beam onto an illuminated region of the fundus; a receiving path for viewing the illuminated region of the fundus where the transmission and receiving paths are configured so that the illuminated region of the interior of the eye external to the fundus is not included in the receiving path, thereby preventing light scattered by the illuminated region of the interior of the eye external to the fundus from obfuscating the image of the fundus:

a cylindrical drum formed about a central axis, said cylindrical drum defining drum side walls defining a transmission slit and a receiving slit;

means for focusing an image of said drum side walls on the fundus of the eye;

means for rotating said drum about the central axis to scan the fundus with said transmission slit and receiving slit;

a segmented light detector for measuring the horizontal and vertical position on the detector of a light beam incident thereon;

a beam splitter for diverting a portion of the receiving path to said segmented detector whereby the rotation of the drum causes the diverted portion of the receiving path to sweep across the segmented detector;

means for measuring the location of the diverted portion of the receiving path on the segmented detector when the rotating drum passes the transmission slit and receiving slit through said transmission path and receiving path to determine the horizontal and vertical errors in eye positions; and means for measuring the rate at which said position beam sweeps across said segmented detector to determine the axial error in eye position.

* * * * *